United States Patent [19]

Bertheussen

[11] Patent Number: 5,045,454

[45] Date of Patent: * Sep. 3, 1991

[54] SERUM-FREE GROWTH MEDIUM AND USE THEREOF

[75] Inventor: Kiell Bertheussen, Eidkjosen, Norway

[73] Assignee: Medi-Cult A/S, Denmark

[*] Notice: The portion of the term of this patent subsequent to Sep. 3, 2008 has been disclaimed.

[21] Appl. No.: 484,557

[22] Filed: Feb. 23, 1990

Related U.S. Application Data

[63] Continuation of Ser. No. 142,069, Jan. 11, 1988.

[30] Foreign Application Priority Data

Jan. 9, 1987 [NO] Norway ............................ 870095

[51] Int. Cl.$^5$ .......................... C12Q 1/02; C12N 5/02
[52] U.S. Cl. .................................. 435/29; 435/240.31
[58] Field of Search .............................. 435/240.31, 29

[56] References Cited

U.S. PATENT DOCUMENTS 4,520,020  5/1985  Loebenstein et al. .

FOREIGN PATENT DOCUMENTS 0174155 12/1986 European Pat. Off. .
3007780  6/1986 Japan .

OTHER PUBLICATIONS

Iscove et al., (1978), *J. Exp. Med.*, 147:923-33.
Sato, Pardee and Sirbasku, eds.; Ham, R. G., (1982), In: *Growth of Cells in Hormonally Defined Media, Cold Spring Harbor Conference on Cell Proliferation*, 9:39-60.
Barnes, et al., (1980), *Anal. Biochem.*, 102:255-70.
Jakoby and Paston, eds.; Ham, et al., (1979), "*Methods in Enzymology, and Growth Requirements*", LVIII:51-2.
Kruse, et al., (1973), *Tissue Culture Methods and Applications*, Section XIV, 671-97.
J. R. Stein, (1973), *Handbook of Physiological Methods*, 1:7-51.
*The Merck Index*, 10th ed. (1983), pp. 330-331.
Bertheussen et al., (1989), *Human Repro.*, 4(5):531-5.
Kirk-Othmer, *Encyclopedia of Chemical Technology*, vol. 19:511, 563-4.
Nielsen, et al., (1989), *Cytotechnology*, Supp. 79.

*Primary Examiner*—Jacqueline Stone
*Assistant Examiner*—George C. Elliott
*Attorney, Agent, or Firm*—Arnold, White & Durkee

[57] ABSTRACT

The present invention discloses a serum-free growth medium with iron-enhancing cell culture characteristics provided by a transferrin-replacing substance. The transferrin replacement preferably comprises an iron-chelate, aurintricarboxylic acid and alkali-metal-EDTA. More particularly, the iron-chelate comprises a mixture of citrate/citric acid and Fe/EDTA. Trace elements and growth factors are also included in the disclosed medium.

The growth medium further comprises base culture media. Most preferably, the base media comprise a mixture of RPMI 1640, HEPES and NaHCO$_3$. The growth medium together with a culture of hybridoma eukaryotic cells may be used for quality testing of other growth media, optionally together with a preferred hybridoma cell line from P$_3$U$_1$ tumor cells and B-lymphocytes. This test procedure is provided by way of a containerized kit which includes the serum-free medium and the most preferred fast-growing eukaryotic cell line, hybridoma ECACC 86 112001.

50 Claims, 2 Drawing Sheets

SERUM-FREE GROWTH MEDIUM AND USE THEREOF

The present application is a continuation of Applicant's copending U.S. patent application, Ser. No. 142,069, filed Jan. 11, 1988, upon which priority in the present application is claimed.

FIELD OF THE INVENTION

The present invention relates to a serum-free medium or medium additive which may be used in culturing cells which require iron for growth. More specifically, the present invention relates to the field of transferrin replacements in cell culture media. Methods of preparing a cell-ready serum-free media and for preparing a cell culture media additive are also described.

The invention also relates to the field of cell culture quality control, as the media may be used in a method to test the quality of other growth media, culturing devices or water purity used in cell culture procedures and mediums. Test kits for such toxic substance detection are also included.

BACKGROUND OF TH INVENTION

Industry and research have historically demonstrated a need for serum-free cell culture media. This need stems from the requirement of most cells to have in the culture medium a iron-presenting component. The requirement by most cell types for iron has long been a problem with culturing most cell types. This iron must be presented in an available form to the cell membrane. Such has previously required the addition of transferrin, usually through the addition of serum, to the growth medium. However, the addition of serum, introduces a variety of undesirable effects on the cell culture, as well as presenting uncontrollable variables to the experimental system. Serum containing cell culture media have not been found to provide the ultimate answer to the need for a serum-free experimental in vitro system with adequate iron-presenting properties.

Components added to a culture medium from the inclusion of serum have been found to exert negative effects on the accuracy of in vitro test results. Many disciplines within the biological arts, such as cellular immunology, biotechnology, in vitro fertilization, organ transplants, I0 cancer research and storage and transfusion of blood products, require that an in vitro system be developed which eliminates serum-related negative effects for a more accurate and reliable test system..

Research in the field has experienced a stand still. Those media and physiological solutions which today are used in in vitro research, industry and in clinical work, are based on antiquated standard formulations, some having been developed as long as 100 years ago. Standard cell culture media preparations routinely include a commercial base medium to which is added approximately 10% heat-inactivated serum. This standard practice of adding serum to the media, however, imparts the following disadvantages to the experimental system:

(1) The heat treatment which is necessary to prevent the lytic effect of the serum on cells has a denaturing effect on important serum components.
(2) Different serum batches have different properties on account of their origin, something which adds unwanted variations to the behavior of the cell cultures in vitro.
(3) Serum contains several unknown factors and compounds with an unknown and uncontrolled effect on cells.
(4) Serum is an unphysiological fluid for most cells since the cells are adapted to the so-called tissue-fluid in the body, whereby this fluid has a different content of different compounds compared to serum.
(5) Antibodies in serum may bind to cells to interfere with experiments.
(6) Serum prevents the study of the cell's synthesis of serum factors in vitro since the "background level" of serum factors is relatively high.
(7) Serum factors act as ligands to bind and thereby mask the undesirable effects of toxic substances, thereby preventing the detection of such toxic substances in the media.

The main problem of previous serum-free media is that they are not suitable for application to a randomly chosen cell culture on account of two circumstances:

(1) The presence of a physiological amount of bicarbonate and $Ca^{2+}/Mg^{2+}$-ions will precipitate iron and trivalent trace metals from almost any known chelator system at 37° C. and pH 7–8 (except transferrin). (Applicant's unpublished work).
(2) The concentration of trace metals including toxic compounds in a medium is not controlled, and will vary significantly depending on the composition and the individual properties of the water and impurities therein. The only solution to this problem is to produce a completely stable metal ion buffer comprising a balanced solution of all the necessary trace elements and metals, and thus the toxic metals will be absorbed by the buffer (the toxic effect will become balanced away).

The use of chelating agents in biological systems to produce metal-ion buffers which act to maintain low levels of free metal-ion concentrations, as well as metal-ion indicators in analytical chemistry is well known.

Control of the quality of embryo growth is of particular io importance in any in vitro fertilization (IVF) program. Therefore, testing of culture media, water quality, equipment, calculating surfaces and other implements involved in cell culture is important. So far, this has only been possible using the mouse embryo test (Ackerman, et al., (1985); Davidson, et al. (1988)). However, this test is a complicated and time-consuming procedure. Furthermore, the reproducability and sensitivity of this test may be questioned. Thus, the need for a simple and sensitive method of quality control continues to exist in the art of in vitro fertilization technology.

SUMMARY OF THE INVENTION

The present invention presents the surprising and unexpected results achieved in cell culture from the addition thereto of a novel transferrin replacement substance which functions to effectively present iron to the cell in the absence of serum, or other substance which may act to present iron to the cell.

The present invention also discloses a new bioassay which satisfies the need for a simple and sensitive alternative method for IVF quality control. This bioassay (Medi-Cult ® Hybritest, GEA Ltd., Biotech Division, Hvidovre, Denmark) is based on the culture of mouse hybridoma cells in the novel serum-free culture medium and transferrin replacement described in the present invention. The main principle of the test is the fact that cells become more sensitive to toxic substances when cultured under serum-free conditions, due to the absence of serum binding proteins. Such binding proteins act to bind toxic substances, and thus, mask detection of such toxins in the media.

Since transferrin is expensive and species-specific, the medium according to the invention was produced to eliminate transferrin. The media of the present invention is instead based on a Fe/trace-element buffer of synthetic non-protein chelators. The main media problem, precipitation of metals at 37° C., was solved by adding certain chelators which, when mixed together in solution, have very different and unique properties compared to each chelator alone.

The problem of presentation of iron to the cell membrane is solved by the present invention through the addition of the particular tricarboxylic acid, aurintricarboxylic acid, to an iron-containing base culture medium together with a non-toxic iron chelate. This combination has been found to support and promote cell growth equally as well as any serum-containing cell culture medium.

As a complete cell culture media suitable for the culture of cells, the present invention in a most preferred embodiment comprises a non-toxic iron chelate wherein iron is present in the concentration interval of about 1-10 $\mu$M, a surplus of one or more non-toxic chelators and citric acid/citrate in a concentration which is at least three times as great as the total concentration of the chelator. An especially preferred concentration of aurintricarboxylic acid in the above described embodiment is within the concentration interval of 0.5-6 $\mu$M.

The most preferred chelators (i.e., chelating agent) of the present invention are EDTA (ethylenediaminetetraacetic acid) and citrate buffer. The most preferred molar ratio of EDTA to citrate buffer is about 1 part EDTA to about 10 parts citrate buffer, or greater by molar concentration. In a most preferred molar ratio, the molar ratio of EDTA to citrate buffer is about 1 part EDTA to about 3 parts citrate buffer. In this respect, it is understood that the citrate buffer represents the sum of citrate and citric acid.

Most preferably, the iron chelate of the present invention comprises the metal chelate complex defined as Fe—EDTA (Fe attached to or coupled with EDTA), together with citrate buffer. A molar ratio between EDTA and citrate buffer (citric acid/citrate) or respectively 1:10 was preferred in oonnection with cell growth, to ensure maximum stability of iron. In a most preferred embodiment, the serum-free growth medium is defined as comprising the metal chelate complex of Fe—EDTA together with citrate buffer in a molar ratio of about 1 part Fe—EDTA:3 parts citrate buffer.

It has been found that aurintricarboxylic acid will present iron to the cell membrane equally as well as transferrin, thus eliminating the need to add transferrin-containing serum to the growth medium. Other tricarboxylic acids, such as PQQ, are not known to possess iron-presenting properties to the cell membrane. Indeed, prior to the present invention, it was unknown that aurintricarboxylic acid possessed iron-presenting properties in vitro. Even where EDTA/citrate made the metal solution completely stable, different animal or human cells did not often grow because of iron deficiency. It was found that the combination of EDTA/citrate buffer and aurintricarboxylic acid provided outstanding chelating and iron presenting properties which previously had not been described.

EDTA has previously been used alone as an iron chelator for growth of plant cells at pH 5.0 under conditions where metal precipitation does not represent any problem.[4] In contrast, the present invention employs EDTA as an iron chelator, in conjunction with citrate buffer, as a solution where metal (i.e., iron) precipitation had been a significant problem in the culture of eukaryotic cells at pHs of between about 7.0-7.8.

Cell growth in media preferably requires a media pH of between about 7.0-7.8,, most preferably at a pH of about 7.4. However, the pH in the final medium according to the present invention may vary, depending on the growth requirements of the particular cell type being cultured.

The disclosed medium has additionally been found to be well suited for culturing and storing cells and tissue in vitro. The complete medium according to the invention is serum-free, essentially protein-free (except for possibly a small quantity of insulin which is required by some cells, and which is included in the disclosed medium where necessary), contains iron and trace elements as stabilized, chelated elements or compounds, and is without transferrin or lipid being present. The medium according to the present invention also possesses the feature of being very inexpensive to produce.

A transferrin replacement for the culture of eukaryotic cells is disclosed in the present invention comprising aurintricarboxylic acid, citrate buffer and EDTA. Aurintricarboxylic acid has been found to present iron to the cell membrane as well as transferrin. Almost any concentration of aurintricarboxylic acid in the growth medium is expected to impart the described iron-presenting properties to the medium. The described transferrin replacing invention may comprise a concentrated solution or concentrate, or a cell-ready culture medium. As a concentrate, the concentration of aurintricarboxylic acid in the cell culture medium is within the range of about 0.1-10 millimolar (mM). A more preferred range of aurintricarboxylic acid in the cell media concentrate or media additive is between about 2.4-3.6 millimolar (mM). An even more preferred concentration of aurintricarboxylic is about 3 millimolar (mM).

The EDTA and citrate buffer (citrate/citric acid) of the disclosed transferrin-replacement cell media concentrate or media additive is further defined as comprising about 2.4-3.6 mM (millimolar) Fe—EDTA, about 0.8-1.2 mM (millimolar) Na$_2$—EDTA, about 12-18 mM citric acid and about 20-30 mM (millimolar) Na$_3$ citrate.

In order to avoid iron precipitation from solution, it is necessary to add particular chelating agents to the medium. Most preferably, these chelating agents comprise EDTA and citrate buffer (i.e., citric acid/citrate). The citrate buffer is not added to adjust the pH, but instead to function as a chelator (although it may incidently have pH adjusting properties). While EDTA is a preferred chelating agent to be used in the disclosed medium, any biocompatible chelating agent (and several are known in the art of cultivating cells) may be used for a similar function. The main consideration is that aurintricarboxylic acid presents the iron in solution to the cell membrane. The concert of EDTA, citrate buffer (i.e., citrate/citric acid) and aurintricarboxylic acid act to comprise a serum-free cell culture medium with synergistically enhanced cell iron-presenting properties.

The disclosed media is provided both as a complete medium as well as a media additive. As defined in the present application, the terms media additive or media concentrate may be used interchangeably, and refer to preparations which must be diluted in some manner before cells may be readily cultured therein. The media additive or concentrate is to be used in conjunction with any base cell culture medium to provide a cell-ready, enhanced iron-presenting medium. For such a diluted cell-ready culture medium, the pH must be adjusted to between 7.0 to 7.8 in order to accommodate cell growth.

The serum-free growth medium additive or concentrate of the present invention in a more preferred embodiment comprises a dry-matter composition. As noted above, the described media additive is in the form of a concentrate, most preferably a 1,000 × concentrate.

As used in this application, the term "cell-ready" medium refers to a medium suitable in pH, molarity and ingredient concentration to support the growth and culture of eukaryotic cells directly therein. Thus, the media additive or concentrate of the present invention is a concentrated solution, and must be diluted appropriately and the pH adjusted sufficiently prior to culturing cells therein.

Most preferably, the base cell culture medium of the present invention comprises RPMI 1640, HEPES and $NaHCO_3$. These components are preferably included at a concentration of 20 mM HEPES and about 2.5 g/L $NaHCO_3$. The medium and medium additive or concentrate also preferably comprise trace elements, which include $Zn^{2+}$, $Cu^{2+}$, $Al^{3+}$, $Cr^{3+}$, $Co^{2+}$ and $Se^{4+}$. The medium may further comprise growth factors, which include pluronic F68, D-glucose, L-glutamine, Na-pyruvate, insulin and ethanolamine.

The present invention also comprises a method for preparing the disclosed enhanced iron-presenting medium or medium additive or medium concentrate. Briefly, the method for preparing a 1000× concentrated serum-free cell cult medium additive comprises preparing a solution A, comprising about 20 mg/ml Pluronic F 68, about 4 mM EDTA, about 3 mM Fe, about 40 mM sodium citrate/citric acid, about 3 mM aurintricarboxylic acid and about 1% trace elements; preparing a solution B, comprising about 0.5 mg/ml insulin; and preparing a solution C, comprising about 20 mM ethanolamine.

More particularly, the 1% trace elements in solution A comprise a stem solution of elements, Mn (about 1 µm), Cr (about 1 µM), Zn (about 0.1 mM), Ni (about 0.2 µM), Co (about 0.2 µM), Cu (about 20 µM), Al (about 2 µM), and Se (about 10 µM).

To prepare a cell-ready culture media, Q. S. (1 ml sol. A + 1 ml sol. B + 1 ml sol. C) with a modified RPMI 1640 medium to 1000 ml, and then adjust the pH to 7.0–7.8. The modified RPMI 1640 medium of the present invention is outlined in Example 1, and Table 4.

Additionally, the present invention comprises a simple and sensitive bioassay method for the detection of impurities and toxic substances in a test material. The elimination of the need for serum in the medium presents tremendous advantages, as the use of serum-free conditions greatly increases cell sensitivity to toxic substances due to the absence of serum binding proteins. Impurities and toxic substances may be detected with the present method in a culture medium or water, or on a surface, particularly a cell culture surface. The bioassay employs the described medium and a culture of fast-growing eukaryotic cells. While a variety of fast-growing cells may be used in conjunction with the assay, the most preferable cells are the eukaryotic hybridoma cells deposited by Applicant, ECACC Deposit No. 86112001. The subject bioassay or test may also be used to detect chemicals which have nothing to do with iron.

In its broadest embodiment, the method for detecting the presence of a toxic substance or impurity in a test material comprises adding a sample of the test material to a volume of iron-containing serum-free cell culture medium containing aurintricarboxylic acid and an iron chelate to form a combination cell culture medium; adding hybridoma cells to the combination cell culture to form a test culture, preparing a control culture comprising an iron-containing serum-free cell culture medium comprising aurintricarboxylic acid and an iron chelate and hybridoma cells, incubating the test culture and the control culture, and comparing hybridoma growth in the test culture to growth observed in the control culture. Greater hybridoma growth in the control culture than in the test culture indicates the presence of a toxic substance in the test material. An equal amount of growth (no difference in hybridoma cell count) indicates the absence of toxic substances in the test material.

The control culture and the test culture must be incubated a period sufficient to discern a detectable difference in cell growth between the cultures. Most preferably, the hybridoma cells comprise the hybridoma cell line deposited by Applicants' ECACC #86 112001.

Equal hybridoma growth in the test culture and the control culture indicates the absence of a toxic substance in the test material. Observed hybridoma growth in the control culture that is greater than observed hybridoma growth in the test culture indicates the presence of a toxic substance in the test material.

The bioassay or test of the disclosed invention in a most preferred embodiment comprises a test kit. By way of example, the disclosed test kit may be employed as a quality control test for the media, water or surfaces (i.e., equipment, cell culture flasks, pipettes, etc.) used in in vitro fertilization.[6] While the subject test may give information about whether a toxic compound is present or absent, it does not identify the type of toxic compound per se. However, successful identification of the particular toxin is possible where a specific toxin is simultaneously employed in conjunction with the described test.

More particularly, the subject test may be used for determining the suitability (toxicity) of materials (e.g. plastic) which are to be used biologically or medically (i.e., together with equipment of other materials, methods or metal alloys, rubber, etc.).

As a method for testing for the presence of a toxic substance in a test material, such as an unknown cell culture medium, the described method in a particularly preferred embodiment comprises first preparing a serum-free, iron-containing cell culture medium comprising aurintricarboxylic acid, iron, and a non-toxic chelating agent in a sufficient volume of a base cell culture medium to prepare a test culture and a control culture. A portion of the serum-free cell culture medium is then to be added to a volume of the unknown cell culture medium to form a toxin detecting concentration of a combination cell culture medium.

A number of hybridoma cells ECACC #86 112001 are then to be added to the combination cell medium to form a test culture. An equal number of hybridoma cells ECACC #86 112001 are also to be added to a volume of the serum-free cell culture medium to form a control culture. Most preferably, the number of hybridoma cells to be added to the test culture and the control culture is approximately 30,000 cells/ml of the particular culture media. The test culture with hybridoma cells and the control culture with hybridoma cells are then to be incubated for a period of time.

After incubation, the number of hybridoma cells present in the test culture and the number of hybridoma cells present in the control culture are to be counted. The number of hybridoma cells counted in the test culture, or test culture hybridoma cell count, is then to be compared to the number of hybridoma cells counted in the control culture, or control culture hybridoma cell count. An equal hybridoma cell count in the test culture to the hybridoma cell count in the control culture indicates the absence of any toxic substance or impurity in the unknown cell culture medium or test sample. The presence of a toxin or impurity in the unknown cell culture medium is indicated where there is a greater number of hybridoma cells in the control culture than there are in the test culture.

As used in the present invention, a "toxin-detecting" concentration or dilution of combination cell culture medium comprises any dilution of an unknown culture medium (in the serum-free culture medium) which provides a detectable concentration of unbound-toxic substances in the combination cell medium. Preferably, the ratio of (v/v) unknown medium:serum-free culture medium is between 1:10 to 10:1 (v/v). Most preferably, the ratio (v/v) of unknown medium: serum-free culture medium is 1:5 to 5:1 (v/v). In an especially preferred embodiment of the claimed method, the combination cell culture medium comprises a ratio (v/v) of unknown medium:serum-free culture medium (v/v) of about 1:1 (v/v). The described dilutions of test material, such as an unknown cell culture medium, provide for the detection of toxic substances therein as the presence of even a trace amount of a toxic substance will elicit a decrease in cell growth compared to control cultures.

The incubation period need only be long enough so as to allow for the detection of a difference in the growth observed between a control culture and a test culture. Most preferably, the period of time over which the test culture and the control culture are to be incubated is about 4 days.

The hybridoma cells of the described method may be supplied either frozen or growing in culture. The serum-free cell culture medium of the described method in an even more preferred embodiment is a modified RPMI 1640 medium comprising between about 2-3 g/L NaHCO$_3$ and between about 10-20 mM HEPES. In a most preferred embodiment, the modified RPMI 1640 medium comprises about 2.2 g/L NaHCo$_3$ and about 15 mM HEPES.

It is recognized that the dilution of the test material will decrease the concentration of any toxic substance in an unknown cell culture medium. However, the described method remains effective owing to the enhanced sensitivity of the described hybridoma cells to the presence of even trace concentrations of a toxic substance or impurity. The presence of any trace amount of a toxic substance in a cell culture medium or other liquid (i.e. water) would manifest a decrease in the observed growth of hybridoma cells cultured therein compared to hybridoma growth in a control culture. As will be recalled, any decrease in the number of cells in a test culture indicates the presence of a toxic substance or impurity in the test material.

The present method is well suited for the detection of toxic substances or impurities in serum-containing media, but only when the test is performed prior to the addition of serum, to avoid toxin-masking effects of serum proteins. Again, the presence of such a toxic substance would manifest a decrease in the number of hybridoma cells in the test culture compared to the number of hybridoma cells in a control culture.

The presence of virtually any toxic substance or impurity may be detected with the above described method. By way of example and not limitation, these substances include heavy metals (Hg, Cd, Pb), phenolic compounds, detergents, (an incomplete list is provided by way of example in the Kirk-Othmer "Encyclopedia of Chemical Technology", 2d ed (1969), 19:511, 563-64, said reference being specifically incorporated herein by reference (in pertinent part), bacterial toxins, formalin, hydrazine, cetyl-pyridinium chloride, lidocaine, caffeine, ethylene glycol and orphenadrine hydrochloride. Other impurities include pollutants, especially those present in water, and raw materials especially those which are used in the production of media. Bacterial toxins include exotoxins such as botulin toxin and diphtheria toxin.

The present invention in a further embodiment comprises a test kit which includes the inventive medium. Specifically, the kit disclosed with the present invention provides for the detection of toxic substances or impurities in a eukaryotic cell culture medium. The kit in a most preferred embodiment comprises a carrier being compartmentalized to receive at least three container means and at least one culture plate in close confinement therein, a culture plate comprising a plurality of wells, a first container means containing an iron-containing, serum-free cell culture medium composition with aurintricarboxylic acid, a second container means containing hybridoma cells, ECACC #86 12001, and a third container means containing a 2× concentrated iron-containing serum-free cell culture medium with aurintricarboxylic acid (as described at Example 6 for RPMI-SR3 at a 2× concentration). Most preferably, the concentrated serum-free culture medium is a modified formulation of RPMI 1640 which includes about 2.5 g/L NaHCO$_3$ and about 15 mM HEPES.

The described kit may, in a more preferred embodiment, further comprise a fourth container means containing sterile tissue culture water. Of course, in such an embodiment, the carrier is compartmentalized to receive at least four container means.

The hybridoma cells ECACC #86 112001 can be supplied in the kit frozen or growing in culture. Most preferably, the carrier and container means which are included with the claimed kit comprise plastic (i.e., a biocompatible plastic material) or any other material suitable for containing biological reagents.

The term "toxic substance" or "impurity" as used in this application is defined as any test material which, when in a cell culture medium, decreases the ability of the hybridoma cell culture to survive or replicate relative to a control culture of hybridoma cells (i.e. toxin-free or impurity-free culture). The term "test material" as used in this application is defined as any cell culture medium, cell culture surface conditioned medium or other fluid (e.g. water) being tested for the presence of toxic materials or impurities, especially as that term is used in the above-described methods.

The following abbreviations are used throughout the Specification:

ATA = aurintricarboxylic acid
DTPA = Diethylenetriaminepentaacetic acid
EDTA = Ethylenediaminetetraacetic acid
EGF = epidermal growth factor
FGF = fibroblast growth factor
HEDTA = N-Hydroxyethylethylenediaminetriacetric acid
HSA = human serum albumin
mM = millimolar
$\mu$M = micromolar
$\mu$g = microgram
mOSM = milliOsmolarity
ng = nanogram
SSR = Synthetic Serum Replacement

DETAILED DESCRIPTION OF THE PREFERRED EMBODIMENTS

The present invention is directed towards a cell culture media or derivatives thereof, for establishing and cultivating animal cells in the absence of serum. More particularly, the invention is directed to a cell culture medium containing a serum replacement which provides iron presenting properties for cells in culture. Typically, serum is added to a cell culture media in order to provide transferrin to the cells being cultured. Transferrin then functions to present iron molecules in the medium to the cell membrane.

Unfortunately, the addition of serum includes the addition of unknown factors to the growth medium which elicit unwanted variations to the behavior of the cell cultures in vitro, as well as the addition of serum antibodies which bind to cells and interfere with experiments. Additionally, the presence of serum in the medium may act to mask experimental responses of the cells in vitro or to enhance these responses artificially. The presence of binding proteins when serum is added to a culture media is also known to decrease the sensitivity of cells to toxic substances. The present invention eliminates these problems through the surprising discovery of a transferrin replacement which acts both to prevent the chelation of iron in the medium and to present the iron in solution to the cell.

A serum-free medium with enhanced iron-presenting properties is provided in the present invention as a complete cell culture medium ready for the culture of cells or a cell culture media additive or concentrate. As a cell-ready culture medium with enhanced iron-presenting properties, the medium comprises aurintricarboxylic acid at a concentration of between about 1-10 $\mu$M final concentration, together with an iron chelate and iron. Even more preferably, aurintricarboxylic acid is included at a concentration between about 1-5 $\mu$M final concentration. In the most preferred embodiment of the cell-ready culture media having enhanced iron-presenting properties, the final concentration of aurintricarboxylic acid is about 3 $\mu$M.

The cell culture media additive or concentrate may preferably comprises a 10$\times$ or a 1000$\times$ concentration of aurintricarboxylic acid (of about 30 $\mu$M = 10$\times$ 3 mM = 1000$\times$) and a non-toxic iron chelate relative to the culture-ready medium. Most preferably, the iron chelate of the present invention comprises a metal-EDTA and a citrate buffer. The citrate buffer comprises a mixture of citric acid and citrate.

Even more particularly, the serum replacement comprises a non-toxic iron chelate and the tricarboxylic acid, aurintricarboxylic acid. Surprisingly, aurintricarboxylic acid (ATA) has been found to facilitate the presentation of iron to the cell membrane as effectively as transferrin-containing serum supplemented media. This effect is to be achieved by adding almost any concentration of aurintricarboxylic acid to the cell culture medium. More particularly, the preferred range of aurintricarboxylic acid in the described cell culture medium concentrate comprises a 1000$\times$ concentrate as a 1000$\times$ concentrate, aurintricarboxylic acid comprises between 0.1-10 mM (millimolar) in the concentrate. An even more preferred preferred concentration of aurintricarboxylic acid of the present invention is about 3 mM (millimolar).

The transferrin replacement of the present invention may further comprise chelating agents. Preferably, these chelating agents comprise citric acid/citrate and EDTA. These chelating agents act to preserve iron in a form which avoids the iron precipitating from the solution. Thus, the citric acid is added as a chelator, rather than to adjust the pH of the medium. While EDTA is a preferred chelating agent of the inventive medium, any biocompatible chelating agent 10 may be used in the media to produce similar effects. Preferably, the complete medium includes the following concentrations of Fe-EDTA, Na$_2$-EDTA, citric acid and Na$_3$-citrate:

about 2.4-3.6 micromolar Fe—EDTA;
about 0.8-1.2 micromolar Na$_3$—EDTA;
about 12-18 micromolar citric acid; and
about 20-30 micromolar Na$_3$-citrate.

The cell culture medium further comprises a cell culture base medium. While any eukaryotic cell base medium may be used in the present invention, the most preferred iron-containing base cell culture medium comprises a mixture of RPMI 1640 NaHCO$_3$ and HEPES. The complete medium most preferably includes about 2.2 g/L NaHCO$_3$ and about 15 mM HEPES.

A particularly preferred embodiment of the present media comprises an iron-containing base cell culture medium, aurintricarboxylic acid, trace metals and an alkali-metal EDTA. While any alkaline or alkaline-rich metal for the alkali-EDTA may be used in the present invention, those most preferred include the alkaline metal sodium (Na) or potassium (K). For example, where sodium is the alkaline metal selected, the alkali-metal EDTA may be specified as EDTA-disodium salt or Na$_2$-EDTA.

The complete medium may further comprise growth factors. By way of example, these growth factors comprise Pluronic F 68, D-glucose, L-glutamine, Na-pyruvate, insulin and ethanolamine. Additionally, the medium may comprise trace elements. By way of example, these trace elements include $Zn^{2+}$, $Cu^{2+}$, $Mn^{2+}$, $Ni^{2+}$, $Al^{3+}$, $Cr^{3+}$, $CO^{2+}$ and Se. These particular trace elements are preferably included in a 1000$\times$ stock solution comprising the following ingredient concentrations:

0.08-0.12 millimolar $Zn^{2+}$;
about 16-24 micromolar $Cu^{2+}$
about 1.60-2.4 micromolar $Al^{3+}$;
about 0.8-1.2 micromolar $Cr^{3+}$;
about 0.16-0.24 micromolar $Co^{2+}$;

about 8-12 micromolar $Se^{4+}$;
about 0.2 micromolar $Ni^{2+}$; and
about 1.0 micromolar $Mn^{2+}$.

The following Examples demonstrate particular aspects of the present invention and particularly preferred embodiments thereof, but do not limit the scope of the claims.

EXAMPLE 1

Serum-Free Cell Culture Medium

Growth medium according to the present invention may be produced, by way of example, by adding a concentrated solution of each of the components listed below to a volume of sterile water (Q.S. to 1000 ml.). It is of great importance to use water of highest possible purity, such as for instance "Travenol" sterile water, when making the medium according to the invention. An example of such a concentrated mixture is given below, where there is produced a composition which may be used as a 1000-fold (1000×) concentration:

|       |                                    | Weight per 100 ml water |
|-------|------------------------------------|-------------------------|
| 3 mM  | Fe-EDTA[1]                         | 120.1 mg                |
| 3 mM  | Aurintricarboxylic acid[2]         | 126.7 mg                |
| 1 mM  | Na$_2$-EDTA                        | 37.2 mg                 |
| 15 mM | Citric acid                        | 315.0 mg                |
| 25 mM | Na$_3$-citrate                     | 735.0 mg                |

[1] Ethylenediaminetetraacetic acid Fe(III)—Na chelate dihydrate (Koch-Light No. 2529-00).
[2] Sigma A 1895
[3] trace elements given below.

The trace elements of the above-formulation may be, by way of example, as described below. The pH of the composition is preferably adjusted to 4.5–5.0.

Optional addition of trace elements may, as an example, be provided by a stem solution. The given stem solution of trace elements will have a 100,000 fold concentration of the final concentration used in the cell-ready medium. These trace elements, by way of example, preferably include $Zn^{2+}$, $Cu^{2+}$, $Al^{3+}$, $Co^{2+}$, $Se^{4+}$, $Ni^{2+}$ and $Mn^{2+}$. These trace elements and the chelators (EDTA and citrate) may be added prior to adjusting the pH to 5.0 with 5–10 N NaOH. The additional components are then added. The final pH is preferably between 4.0 and 4.5.

TABLE 1

| Trace Metal (conc.) | Salt | Weight per 100 ml water |
|---|---|---|
| 10 mM Zn | ZnSO$_4$ 7H$_2$O | 287.5 mg |
| 2 mM Cu | CuSO$_4$ 5H$_2$O | 49.9 mg |
| 0.1 mM Mn | MnSO$_4$ H$_2$O | 1.7 mg |
| 0.02 mM Ni | Ni(NO$_3$)$_2$ 6H$_2$O | 0.58 mg |
| 0.2 mM Al | NH$_4$Al(SO$_4$)$_2$ 12H$_2$O | 9.2 mg |
| 0.1 mM Cr | KCr(SO$_4$)$_2$ 12H$_2$O | 5.0 mg |
| 0.02 mM Co | CoCl$_2$ 6H$_2$O | 0.48 mg |
| 1 mM Se | SeO$_2$ | 11.1 mg |
| 14 mM Na$_2$-EDTA | | 521.1 mg |
| 1 mM Na$_3$-citrate | | 29.4 mg |

It is of course to be understood that such a composition of trace elements may contain other elements than those which are given in the table above, depending on the requirements of the tissue or cell types being cultured.

The medium according to the invention may, in addition to the components described previously, further comprise growth-stimulating and other necessary compounds for cell growth. Such compounds may comprise for instance the surfactant Pluronic F 68 (20 mg/l), D-glucose (2.0 g/l), L-glutamine (2 mM), Na-pyruvate (1 mM), insulin (0.5 mg/l) and concentration in the cell-ready culture medium.

An additional form of the mentioned compounds (with exception of ethanolamine which is a fluid at room temperature) may be provided as a dry product, and as such may be stored for extended periods of time up to several years.

Ethanolamine may, if required, be added to the medium in the desired concentration when using the composition. Ethanolamine is most often used in experiments with hybridomas and the production of monoclonal antibodies.

A preferred base cell culture medium of the claimed medium or medium additive according to the present invention comprises RPMI 1640, about 2.5 g/l NaHCO$_3$ and 20 mM HEPES (N-2-hydroxy-ethylpiperazine-N-N'-2-ethanesulphonic acid) in the cell-ready medium composition. For purposes of this application, a "cell ready" medium is defined as a culture medium with appropriate nutrient concentrations and suitable pH and molarity to support the growth and culture of eukaryotic cells directly therein. The described medium (SR3) is also present as a 2× concentrate in the described test kit for the detection of toxic substances or impurities in water and eukaryotic cell culture media of low osmolarity, and this 2× concentrate is accordingly diluted 1:1 in the assay.

A preferred cell culture to be used in conjunction with the serum-free medium of the present invention comprises a culture of L 929 mouse fibroblast cell-line, HELA human tumor cell line or various mouse and human B-hybridoma cells. These cell cultures all produce monoclonal antibodies in quantities which correspond to growth in serum-containing cultures and human monocytes which differentiate to developed macrophages during 7 days while keeping their complement receptors.

cEXAMPLE 2

Method for Culture Media Quality Control

An especially preferred use of the present invention is performed with fast-growing cell types for testing the quality or presence of impurities or toxic substances in other types of media. The method comprises mixing the serum-free medium composition according to the invention with RPMI 1640, adding the "test" medium to a volume of the serum-free medium in a ratio of 1:1 to form a combination cell culture medium, adding a number of fast growing hybridoma cells, for example hybridoma cells ECACC #86112001, of approximately 30,000 cells/ml, and incubating the combination medium and cells for a period of time. Most preferably, the period of incubation is 4 days. After the incubation period, the number of cells in the media is determined and the number compared to the number of cells present in a control culture of hybridoma cells incubated in a volume of serum-free cell culture medium alone for the same period of time.

Where there are no toxic substances or impurities present in the unknown cell culture medium, the number of hybridoma cells in the "test" culture after 4 days incubation will be approximately the same as the number of hybridoma cells observed in a corresponding "control" culture in the serum-free cell culture media. If, however, toxic compounds or impurities are present in the unknown medium, there will not be an equal increase in observed hybridoma cell numbers. Thus, only when the cell growth is equally rapid in the test culture as in the control culture containing a pretested control medium (for example, the medium for the Applicant's Hybritest cells, i.e. RPMI-SR3) is an absence of toxicity indicated. This comprises a very simple media quality-control test which is extremely sensitive because it is performed without serum. False results are avoided due to the absence of other serum components which bind and mask toxic substances and impurities in the culture medium being tested.

For purposes of this application, toxic substances or impurities include substances which retard or halt cell growth. By way of example, these substances include antibodies, heavy metals (e.g., Hg, Cd, Pb), phenolic compounds, and detergents. Other media impurities, by way of example include bacterial toxins (e.g., exotoxins such as botulin toxin, diphtheria toxin), formalin, hydrazine, cetylpyridinium chloride, lidocaine, caffeine, ethylene glycol, orphenadrine hydrochloride, water pollutants and raw materials which are used in the preparation of cell culture media.

SURFACE TESTING

In addition, the present tests may be used for determining the suitability of plastic and other biologically compatible materials which are to be used biologically or medically (together with equipment of other materials, metals or metal alloys, rubber, etc.) by detecting the present of toxic substances or impurities on a surface. The method for detecting the presence of toxic substances or impurities on a surface according to the present invention comprises incubating the surface to be tested in a volume of medium comprising RPMI-SR3 (See Example 6), preferably for about 1 hour to obtain a volume of conditioned RPMI-SR3 medium. To a volume of this conditioned RPMI-SR3 medium is then added a number of hybridoma cells (most preferably, 30,000 cells/ml cell culture medium). Most preferably, these hybridoma cells comprise the hybridoma cell line deposited with the ECACC #86 112001. The hybridoma cells are incubated in the conditioned RPMI-SR3 medium, most preferably for about 4 days.

At the end of the incubation period, the number of hybridoma cells grown in the conditiŏned medium is counted and compared to the number of hybridoma cells cultured from the same number of starting hybridoma cells in a control culture in a volume of serum-free cell culture medium incubated for the same period of time. A lower number of hybridoma cells cultured in the conditioned media compared to the number grown in the control or "non-conditioned" RPMI-SR3 media indicates the presence of toxic substances on the surface being tested. An equal number of cells in the "conditioned" RPMI-SR3 medium relative to the number grown in "unconditioned" medium over the same incubation period indicates the absence of toxic substances or impurities on the cell culture surface. Most preferably, the surface tested in the above toxic substance detection method is a cell culture surface.

EXAMPLE 3

Comparative Chelating Agent Studies in Serum-Free Cell Culture Medium

The present experiment was devised to compare the effectiveness of various chelating agents in a serum-free eukaryotic cell culture medium.

A four day old culture of hybridoma "hybritest" cells (1E6) in RPMI-SR3, wherein EDTA has been exchanged with two other chelators in equal concentrations, was prepared. A culture of $3 \times 10^4$ cells/ml cells was seeded in each experimental culture system. Cells were counted in each experimental culture system after 4 days incubation. The number of cells obtained in each system is shown below.

TABLE 2

| Cell Count After 4 days | |
|---|---|
| EDTA (control) | $3.3 \cdot 10^5$ cells/ml |
| EDTA without iron | $2 \cdot 10^5$ cells/ml |
| HEDTA | $2.9 \cdot 10^5$ cells/ml |
| DTPA | 0 cells |

The data shows that certain different chelators have distinct effects on eukaryotic cell growth in vitro. EDTA was shown to work in the SSR-medium, while HEDTA demonstrated good cell growth. DTPA was shown not to be well suited as a chelating agent in the serum-free medium, as all cells died.

EXAMPLE 4

Comparative STudy of Various Cell Types in Serum vs. Serum-Free Medium with Aurintricarboxylic Acid The present experiment was designed to determine what the optimal concentration of aurintricarboxylic acid for the culture of the described hybridoma cells would be. In the course of these studies, it was found that data relating to dose response of ATA is complicated by many factors.

In the present experiment, the metal ion buffer, including iron, remained constant. The amount of ATA was varied with different types of cells.

TABLE 3

| Conc. ATA[1] | Cell Count | |
|---|---|---|
| | 1E6 4 days[2] | L929 5 days[3] |
| 0 | $0.9 \cdot 10^5$ | $0.5 \cdot 10^5$ |
| 0.1 μM | $1.1 \cdot 10^5$ | $0.7 \cdot 10^5$ |
| 1 μM | $3 \cdot 10^5$ | $3 \cdot 10^5$ |
| 3 μM | $4 \cdot 10^5$ | $5 \cdot 10^5$ |
| 5 μM | $3 \cdot 10^5$ | $3 \cdot 10^5$ |
| 10 μM | $1.3 \cdot 10^5$ | $1.5 \cdot 10^5$ |

[1] ATA - Aurintricarboxylic acid
[2] 1E6 seeded at $3 \cdot 10^4$ /well
[3] L929 seeded at 1 · 10^4 /well

EXAMPLE 5

Comparative Study of Various Cell Types in Serum vs. Serum-Free Medium

To substantiate the effectivness of the growth medium according to the invention, studies were conducted wherein various cell types were cultured in the described novel culture medium without serum. Growth of cells in the novel culture medium without serum was compared to growth obtained of the same cell type in serum-containing medium. Examples of serum-free culturing methodology are shown below. Mother cultures contained serum.

Cell types examined in the present studies included the following:

Vero
Medium: RPMI-SR2 with HSA (Human Serum Albumin) 0.2 mg/ml — 10 ng/ml EGF (EGF most important).
Substrate: Gelatin-coated Falcon plate.
Counting: $5 \cdot 10^3$ /well initially.
$3 \cdot 10^5$ /well after 5 days.

-continued

HeLa
Medium: RPMI-SR2 with HSA 0.2 mg/ml, 50 ng/ml Dexa methasone, 10 ng/ml EGF (EGF most important).
Substrate: Gelatin-coated Falcon plate.
Counting: 1 · 10⁴/well initially.
5.0 × 10⁵/well after 5 days.

HeLa S3
Medium: RPMI-SR2
Substrate: Fibronectin-coated Falcon plate.
Counting: 5 · 10³/well initially.
6 × 10⁵/well after 5 days.

SV-40 3T3
Medium: RPMI-SR2 with HSA 2 mg/ml + EGF 10 ng/ml.
Substrate: Gelatin-coated Falcon plate.
Counting: 2 · 10⁴/well initially.
5 × 10⁵ after 5 days.

Figure 1:
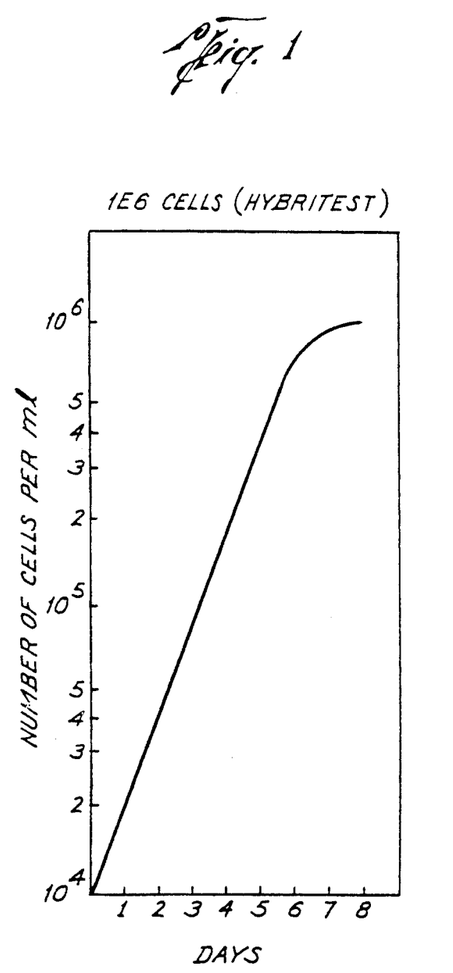
FIG. 1 depicts the growth curve of 1E6 cells in RPMI-SR3 medium.
Figure 2A:
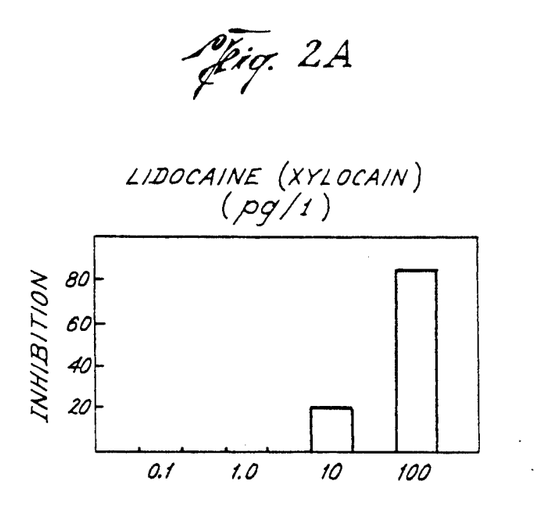
FIG. 2 shows examples of preliminary tests of 1E6 cells in the presence of various chemicals.
Figure 2B:
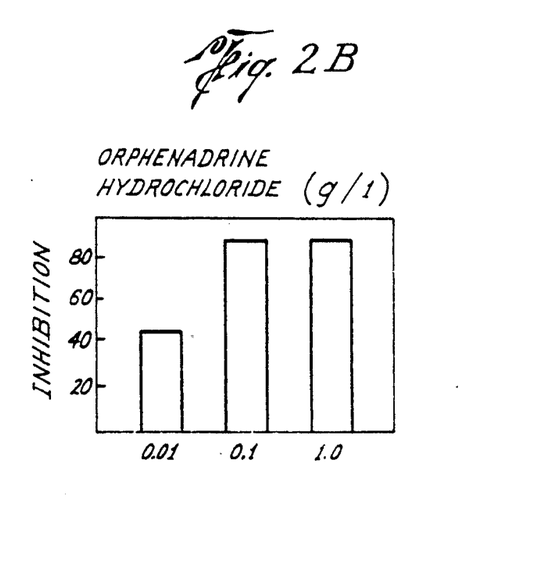
Figure 2C:
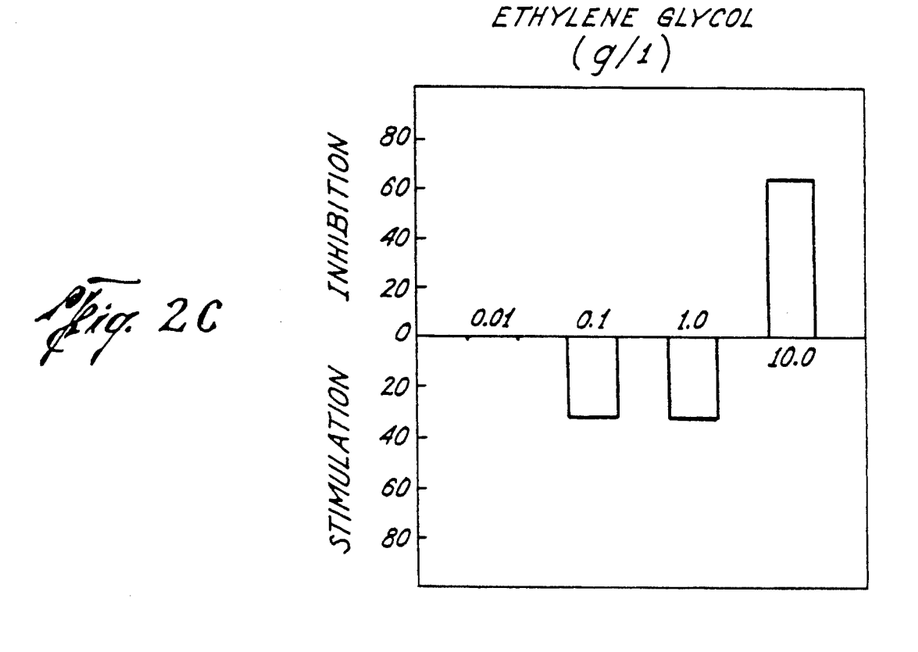
Figure 2D:
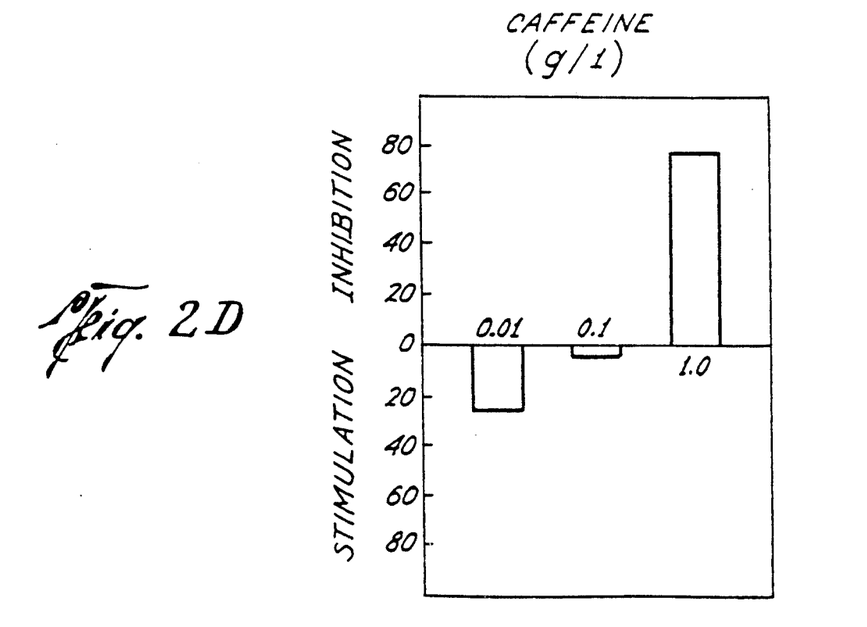

Hybridoma cells (1E6)
(See FIG. 2 and accompanying text in the Inventor's publication "A New Cell Culture Assay for Quality Control in IVF". Human Reprod., 4(5), 531-35, (1989)).

L929
Medium: RPMI-SR2
Substrate: Falcon plate without coating.
Counting: 1 · 10⁴/well initially.
4 · 10⁵/well after 5 days.

3T3
Medium: RPMI-SR2 with HSA 2 mg/ml, fetuin 0.5 mg/ml, 50 ng/ml Dexamethasone, 5 uM Na₃VO₄, 10 ng/ml EGF, 10 ng/ml FGF.
Substrate: Falcon with gelatin-coating + fibronectin.
Counting: 1 · 10⁴/well initially.
1 · 10⁵/well after 5 days.

Human Fibroblasts
Methodology as with 3T3, but they may grow without FGF.
Counting: 2 · 10⁴/well initially.
2 · 10⁵/well after 5 days.

In the above specified tests the abbreviations FGF and EGF denote fibroblast growth factor and epidermal growth factor (peptides) respectively, and HSA denotes human serum albumin. Falcon is a type of culture plate with wells for culturing cells.

Applicant's results from the described studies indicate that the optimal concentrations of ATA is imperative to obtaining the best cell growth. Larger or smaller doses of ATA, while exhibiting some growth, results in limited cell growth at best.

EXAMPLE 6

Quality Control Test Kit

The growth medium according to the present invention together with a fast-growing hybridoma cell type may be incorporated in a test-kit. This test kit comprises, for example, the serum replacement according to the present invention, and frozen or growing cells. The kit may further comprise a base culture medium (RPMI 1640). The kit carrier, container means, and culture equipment of the claimed test kit comprise a plastic or other material suitable for the containment of biological reagents.

The kit is defined further as comprising a carrier compartmentalized to receive at least four container means in close confinement therein. The kit is fitted to receive a first container means comprising an iron-containing serum-free cell culture medium containing aurintricarboxylic acid. A second container means comprises a hybridoma cell line (ECACC #86112001). The hybridoma ECACC #86112001 is characterized as a fast-growing cell line. The expressing "fast-growing" relates to the culture doubling rate of the cells. This is objectively measured by counting the cells in the cultures.

While any fast-growing eukaryotic cell type may be used in conjunction with the present inventive media quality test kit, the most preferred eukaryotic cell comprises a hybridoma cell line which has a culture doubling time (dividing time) of 8 hours in serum-containing medium and 24 hours in serum-free medium.

Principally, any cell type may be used in the practice of the present invention. However, the most preferred cell line comprises a hybridoma cell line ECACC #86 1200, which has been deposited with the following depository:
European Collection of Animal Cell Cultures
Porton Down
Salisbury, Wiltshire SP4 OJG The culture was deposited on Nov. 20, 1986, with Accession Number 86112001. This cell type is a special fastgrowing hybridoma cell type derived from the fusion of $P_3U_1$ tumor cells with mouse B-lymphocytes. This hybridoma cell line has proven to be especially useful for quality testing of other growth media as a fast-growing cell line. The hybridoma (#86112001) comprises a preferred cell line to be used in conjunction with the described methods and particularly preferred media composition of the test kit. The use of any other cell type in conjunction with the present invention will require that the claimed test be changed to optimize the suitability of the media for the biological requirements of the cell type chosen.

The most preferred embodiment of the test kit of the present invention includes the described hybridoma cell line ECACC #86112001. These hybridomas are termed "hybritest" cells, (1E6) and may be included with the described kit in a 1 ml ampoule, in addition to a 100 ml bottle of RPMI-SR3 medium, RPMI-SR3 2× in a 100 ml bottle, a 24-well culture plate and a 100 ml bottle of sterile tissue culture water.

In an even more preferred embodiment of the claimed kit, in addition to the above materials, a 100 ml bottle of RPMI w/equine serum is included. The RPMI with/equine serum is during the actual test, otherwise the cells are cultured/bred in medium with equine (horse) serum. Extra plastic equipment for pipetting is included.

RPMI-SR3 2× is used for testing water and other liquids with an osmolarity virtually equal to zero, so that after a dilution of 1:1, a normal osmolarity is produced, ideally 280 mOsm.

In addition, it is vitally important that the hybridoma Hybritest (1E6) cells are cultured in serum-containing medium since such a medium gives a far greater insurance of absence of toxic compounds. Thereby, the selection of toxicity-resistant mutants (sub clones) of 1E6 is avoided. As will be appreciated, toxicity-resistant mutants in the described test would render the test ineffective in the detection of toxic components.

The described test reagents are particularly preferred in that they optimize both the sensitivity and occurrence of the described detection of cell media contaminants and pollutants.

The Applicant's standard SSR media are based on a modified RPMI 1640 medium. The most preferred modified RPMI 1640 medium of the invention includes ingredients listed in Table 4.

TABLE 4

| | |
|---|---|
| RPMI 1640 powder as specified by ATCC w/o NaHCO₃ | 8.8 g/l |
| NaHCO₃ | 2.2 g/l |

TABLE 4-continued

| | | | | |
|---|---|---|---|---|
| HEPES buffer (from stock pH 7.3) | | | 15 | mM |
| Na pyruvate | | | 88 | mg/l |
| Extra Glucose | | | 1.9 | g/l |
| Extra L-Glutamine | | | 228 | mg/l |
| Penicillin | | | 50,000 | IU/l |
| Streptomycin | | | 50 | mg/l |
| Osmolarity 280 mOsm. | | | | |
| Solution A: | | | | |
| Pluronic F 68 | | | 20 | mg/ml |
| EDTA | | | 4 | mM |
| Sodium citrate/citric acid | | | 40 | mM |
| Aurintricarboxylic acid | | | 3 | mM |
| Trace elements: | | | | |
| Fe  3 mM | Zn | 0.1 mM | Cu | 20 μM |
| Mn  1 μM | Ni | 0.2 μM | Al | 2 μM |
| Cr  1 μM | Co | 0.2 μM | Se | 10 μM |
| Solution B: | | | | |
| Insulin 0.5 mg/ml | | | | |
| Solution C: | | | | |
| Ethanolamine 20 mM | | | | |
| There are three types of SSR concentrations (1000x): | | | | |
| SSR 1 contains solution A | | | | |
| SSR 2 contains solution A + B | | | | |
| SSR 3 contains solution A + B + C. | | | | |
| To make one liter medium, add: | | | | |
| 1 ml A → RPMI-SR1 | | | | |
| 1 ml A + 1 ml B → RPMI-SR2 | | | | |
| 1 ml A + 1 ml B + 1 ml C → RPMI-SR3. | | | | |

To the described modified RPMI 1640 medium outlined in Table 3 are added particular volumes of solution A, solution B, and/or solution C, depending upon the desired final medium desired (i.e., RPMI-SR1, RPMI-SR2, and RPMI-SR3).

Some preliminary growth curves for different types of cells are described in Example 5. Quantification of cultures has been expressed as number of cells at the starting point and end point in standard 16 mm culture wells.

EXAMPLE 7

Quality Control in In Vitro Fertilization Techniques

The present experiment was designed to adapt the presently described toxin-detection system for use in testing the culture media, water and equipment used in in vitro fertilization techniques.

Hybritest (1E6) cells were best maintained in RPMI 1640 (2.2 g/l $NaHCO_3$) with 10% (v/v) horse serum. In this medium, cell number optimally increases 4 times in 24 hours. The minimum initial cell number was $0.1 \times 10^5$ ml and the maximum cell density when passaging was $5 \times 10^5$/ml. A stock suspension of 1E6 cells was cultured in 10 ml culture medium (RPMI 1640; 10% horse serum) in 50-ml culture flasks. (Nuno, Roskilde, Denmark, cat. no. 1-63371) to a cell density of approximately $5 \times 10^5$/ml. The cells were then split to a density of $0.1–0.5 \times 10^5$/ml.

SSR3 medium used in the present studies is described in the Table below.

TABLE 5

Composition of RPMI-SR3

| | |
|---|---|
| RPMI 1640 (powder) | 8.80 g |
| $NaHCO_3$ | 2.2 g |
| Penicillin | 50,000 IU |
| Streptomycin | 50 mg |
| Hepes acid total 15 ml | 2.74 g |
| Hepes sodium salt | 0.91 g |
| Glucose | 1.90 g |
| pyruvate | 0.088 g |
| SSR solutions A, B, C, each | 1 ml |

TABLE 5-continued

Composition of RPMI-SR3

| | |
|---|---|
| L-Glutamine | 0.228 g |
| $H_2O$ (Travenol) ad. | 1000 ml |

TESTING OF CULTURE MEDIA

The testing of culture media was performed as follows:

1. RPMI-SR3 and test medium sample (both 0.5 ml) were mixed in quadruplicate in 16-mm culture wells in a 24-well culture plate (Nunc, cat. no. 1-43982). Care was taken to ensure that the pH and osmolarity remained unchanged (i.e. pH 7.4 and 280 mOsm). This was accomplished by equilibrating the culture plate in the incubator (5% $CO_2$ in air, absolute humidity) for at least 30 min. prior to the addition of cells, and if necessary by addition of $NaHCO_3$.

2. Control medium (RPMI-SR3) was apportioned in quadruplicate in 16-mm wells in the same 24-well culture plate as the test medium sample.

3. Horse serum was removed from the cells by double centrifugation and washing in RPMI Hepes (RPMI 1640 with 350 mg/l $NaHCO_3$ and 15 mM Hepes, GEA BioTech, cat. no. 1071). The cell number was adjusted to $1 \times 10^6$/ml in RPMI Hepes.

4. Cells were added at $1 \times 10^4$/ml (10 ul/well) to the test cultures and controls, and incubated at 37° C. in 5% $CO_2$ in air.

5. Cell counting was performed after 4 days in culture.

TESTING OF WATER

The testing of water was performed as follows:

1. RPMI-SR3 was made up with the water to be tested. RPMI-SR3 2× is prepared according to the following formulation:

RPMI-SR3 2×

1 ml. Sol. A. + 1 ml. Sol. B + 1 ml. Sol. C.
Q.S. to 500 ml for a 2× RPMI-SR3.

RPMI-SR3 2× is used for testing water and other liquids with an osmolarity virtually equal to zero, so that after a dilution of 1:1 a normal osmolarity is produced, preferably an osmolarity of 280 mOsm.

2. The test medium and the control medium (RPMI-SR3 (1×)) were apportioned in quadruplicate in 16-mm wells in the same 24-well culture plate.

3. The horse serum was removed from the cells as described for "culture media", infra, and the cell number adjusted to $1 \times 10^6$/ml in RPMI Hepes.

4. Cells were added to all wells and incubated at 37° C. in 5% $CO_2$ in air.

5. Cell counting was performed after 4 days in culture.

TESTING OF EQUIPMENT

The testing of equipment (i.e. culture dishes, pipettes, catheters, tubes, etc.) was performed as follows.

1. The equipment was kept in RPMI-SR3 (1×) medium for a reasonable period of time, (i.e. corresponding to the time the equipment would be expected to be in contact with the biological materials (oocytes, pre-embryos, sperm)). As a minimum, an exposure time of 5, 10 and 60 min is recommended. Applicants experience with this system indicates that increasing the period of incubation increases the sensitivity of the assay.

2. The different portions of test medium and the control medium were apportioned in quadruplicate in 16-mm wells in the same 24-well culture plate.
3. The cells were handled as described.
4. Cells were added and incubated as described.
5. Cell counting was performed after 4 days.

As a further control the cell culture test may be carried out on RPMI-SR3 medium pre-treated with equipment known to be non-toxic.

TESTING OF CHEMICAL COMPOUNDS

The testing of chemical compounds was performed as follows:

1. A stock solution was prepared from RPMI-SR3 (1×) and the chemical compound to be tested. A series of dilutions were made from this stock solution.
2. The control medium (RPMI-SR3 1×) and samples from the different concentrations were apportioned in quadruplicate in 16-mm wells in the same 24-well culture plate.
3. The cells were handled as described.
4. The cells were added and incubate as described.
5. Cell counting was performed after 4 days in culture.

RESULTS

A cytoxic index (percentage inhibition of cell growth) was calculated using the following formula:

$$(N_2 - N_1)/N_2 \cdot 100$$

wherein $N_1$ is the final cell number in test cultures and $N_2$ the final cell number in control cultures.

The coefficient of variation of the cell number for multiple incubations of identical quadruplicate cultures, i.e., the inter-assay variation of the hybridoma cell culture test, has been found to be <8%. The intra-assay variation was <5%. To avoid the effect of arbitrary variations, the limit of resolution of the test was set to 10% cytotoxicity. Thus, cytotoxicity levels <10% were not regarded as significant and were interpreted as a negative test. At ≧10% inhibition of cell growth, the test was considered positive.

CULTURE MEDIA, WATER AND CHEMICAL COMPOUNDS TESTED

Culture media

Nineteen different batches of culture media were tested, falling into two main categories, ready-made fluid media (nine batches, Table 6a), and media freshly prepared from powder and sterile water (10 batches, Table 6b). The water used was Travenol sterile water (Travenol Laboratories, Thetford, UK).

The different ready-made fluid media showed substantial batch-to-batch variations as regards cytotoxicity in the hybridoma cell test. Most importantly, only two fluid media were found to be non-toxic. On the contrary, the testing of culture media processed from powder and high quality sterile water revealed no inhibition of cell growth.

TABLE 6

| Medium Batch No. | Medium | Source | Cytotoxicity (%) |
|---|---|---|---|
| (a) | | | |
| 1 | EBSS | Sigma | 0 |
| 2 | EBSS | Sigma | 92 |
| 3 | EBSS | Gibco | 32 |

TABLE 6-continued

| Medium Batch No. | Medium | Source | Cytotoxicity (%) |
|---|---|---|---|
| 4 | EBSS | Gibco | 88 |
| 5 | EBSS | Flow | 85 |
| 6 | Ham F10 | Sigma | 100 |
| 7 | Ham F10 | Gibco | 95 |
| 8 | Ham F10 | Flow | 61 |
| 9 | RPMI 1640 | Sigma | 0 |
| (b) | | | |
| 1 | EBSS | Sigma | 0 |
| 2 | EBSS | Sigma | 0 |
| 3 | EBSS | Gibco | 0 |
| 4 | EBSS | Gibco | 0 |
| 5 | EBSS | Flow | 0 |
| 6 | EBSS | Flow | 0 |
| 7 | Ham F10 | Sigma | 0 |
| 8 | Ham F10 | Sigma | 0 |
| 9 | Ham F10 | Gibco | 0 |
| 10 | Ham F10 | Flow | 0 |

WATER

Water from 13 different sources was tested in the hybridoma cell test (Table 7).

TABLE 7

| Type of Water | Cytotoxicity (%) |
|---|---|
| Tap water, ×2 distilled | 35 |
| tap water, ×2 distilled, stored non-sterile | 92 |
| Millipore RO, producer A | 11 |
| Millipore RO, producer B | 0 |
| Pharmacia sterile water, A | 0 |
| Pharmacia sterile water, B | 88 |
| Steridos sterile water | 0 |
| NAF sterile water | 0 |
| Travenol sterile water (UK) | 0 |
| Travenol sterile water (US) | 0 |
| Medipolar sterile water | 0 |
| Analar sterile water | 0 |

The results from testing of different batches of water are shown in Table 7. Double-distilled tap water inhibited cell growth by 35%. By storage under non-sterile conditions the cytotoxicity index increased to 92%. Sterile water processed by the Millipore Reverse Osmosis System (Millipore, Copenhagen, Denmark) showed no inhibition of cell growth in all but one batch, where a cytotoxicity index of 115 was found. On the other hand, water from the Millipore Milli-Q System was found to be non-toxic. With one exception, all industrially processed water batches were found to be non-toxic in the hybridoma cell test (Table 7).

Three known toxic agents were tested: formalin (0.1–1000 uM), cetyl-pyridinium-chloride (0.002–200 uM) and hydrazine (0.5–500 uM). The LD-50s of these substances are 800, 200 and 57 mg/kg respectively. In addition, lidocaine chloride (Xylocain, Astra, Sodertalje, Sweden), a substance in common use as a local anaesthetic for ultrasound-guided follicular puncture, was tested in concentrations from 0.0001 to 0.1 mg/ml.

FORMALIN

The hybridoma cell test was negative, i.e. <10% inhibition of cell growth, using formalin at concentrations of 0.1 and 1.0 uM. By 10 μM formalin, a borderline positive test was found (10.3% inhibition of cell growth). By 100 and 1000 μM formalin the hybridoma cell test was highly positive, i.e. almost 100% inhibition.

CETYL-PYRIDINIUM CHLORIDE

Concentrations of 0.0002 and 0.002 μM cetyl-pyridinium chloride were found to be non-toxic according to the hybridoma cell test. At concentrations ≧0.02 μM an almost complete inhibition of cell growth was observed.

HYDRAZINE

The testing of hydrazine revealed a negative hybridoma cell test by a concentration of <50 μM. At 500 and 5000 μM hydrazine, inhibition of cell growth of 62 and 98%, respectively were observed.

LIDOCAINE

Lidocaine in concentrations of 0.0001 ng/ml and 0.001 ng/ml showed no cytotoxicity. At a concentration of 0.01 mg/ml 20% inhibition of cell growth was observed, whereas a concentration of 0.1 mg/ml was highly toxic (85% inhibition of cell growth).

EXAMPLE 7

The heart of the present invention resides in finding a replacement for transferring (which is aurintricarboxylic acid) together with a component to chelate the iron to make it available to the cell (the chelator). In this regard, the present experiment was conducted to determine the suitability of several different chelators with aurintricarboxylic acid and citric acid/citrate in an iron-containing cell culture media for promoting cell growth. Cell growth in this experiment was indicative of the ability of the particular individual chelator to chelate iron in the media, with the ATA functioning in concert therewith to make the iron available to the cell. EDTA without iron, HEDTA and DTPA were tested as individual chelators.

Applicant's prior use of imino diacetic acid as the chelator was found to result in the inability to prevent the partial precipitation of iron as $Fe(OH)_3$ from the cell media. This chelation of iron in the cell culture media made the iminodiacetic acid become very unstable. This instability of iminodiacetic acid makes it an unsuitable chelator in the present system. HEDTA as a chelator was found to result in sub-optimal growth of cells in culture as compared to cell growth observed with EDTA as the chelator (Table 8). DTPA was found not to be suitable for use as a chelator in the present inventive serum-free cell culture media, as no cell growth was observed at all in cultures containing DTPA alone as the chelator (Table 8).

TABLE 8

| Test for Different Chelators in SSR Medium | |
|---|---|
| | Cell Count after 4 days |
| EDTA | $3.3 \times 10^5$ cells/ml |
| HEDTA | $2.9 \times 10^5$ cells/ml |
| DTPA | 0 |
| EDTA without iron | $2 \times 10^2$ cells/ml |

EDTA was exchanged with the other chelators in equal concentrations. $3 \times 10^4$ IE6 cells/ml were seeded onto each culture. Cells were allowed to culture for four days. Cells present in each culture were then counted.

These studies demonstrated that different chelators may work in the described media with ATA. HEDTA chelator demonstrated inferior, yet some growth of cells, with the EDTA demonstrating the best cell growth. DTPA was shown to be not well suited at all, as all cells in that culture died.

EXAMPLE 8

Cell Ready Serum-Free Iron Containing Cell Culture Media

The following represents the most preferred embodiment of the claimed formulations in a cell-ready, iron-containing cell culture medium. In 1 liter of Modified RPMI iron containing cell culture media is contained:

20 μM ethanolamine (only for hybridoma cells IE6)
0.5 μg/ml insulin (bovine)
20 μg/ml Pluronic F68
4 μM EDTA
40 μM citrate/citric acid
3 μM aurintricarboxylic acid
3 μM Fe
0.1 μM Zn
20 nM Cu
1 nM Mn
0.2 nM Ni
2 nM Al
1 nM Cr
0.2 nM Co
10 nM Se The Modified RPMI 1640 is to be prepared according to the following formula:

1 mM sodium pyruvate
2 mM L-glutamine
2 g/l D-glucose
0.2 g/l $NaHCO_3$ (total 2.2 g/l $NaHCO_3$)

The pH of the above media is then to be adjusted to between 7.0–7.8. Citric acid/citrate (i.e., the described citrate buffer) is added in order to buffer metal ions, and not to adjust the pH. Thus, the citric acid/citrate as a metal stabilizer serves one of the main objects of the present invention to stabilize metal irons when in solution. The ratio between citric acid and citrate is pH dependent, and thus citric acid and citrate is added in a certain ratio to achieve an optimum pH.

The following references are herein specifically incorporated by reference in pertinent part as may be appropriate throughout the present specification:

BIBLIOGRAPHY

1. N. N. Iscove and F. Melchers, "Complete Replacement of Serum by Albumin, Transferrin, and Soybean Lipid in Cultures of Lipopolysaccharide-reactive B-lymphocytes", *J. Exp. Med.* 147:923–933 (1978).
2. R. J. Ham, "Importance of the Basal Nutrient", In: *Growth of Cells in Hormonally Defined Media*, Cold Spring Conference on Cell Proliferation, 9:39–60 (1982).
3. D. Barnes and G. Sato, "Methods for Growth of Cultured Cells in Serum-free Medium", *Anal. Biochem.*, 102:255–270 (1980).
4. P. Krse and M. K. Petterson, "Tissue Culture Methods and Applications", *Acad. Press* (1973); J. R. Stein, "Handbook of Physiological Methods", Cambridge University Press (1973)
b 5. Nielsen, et al., "The Medi-Cult ® Hybritest for In Vitro Toxicology and Quality Control.
6. Bertheussen, et al, (1989), *Human Reproduction*, 4(5):531–35.
7. Nielsen, et al. (1989), *Cytotechnology*, Supp. 1989:79.

8. Kirk-Othmer, (1969), *Encyclopedia of Chemical Technology*, 2nd ed. 19: 511, 563-564

What is claimed is:

1. A serum-free eukaryotic cell growth medium comprising aurintricarboxylic acid, an iron-containing base cell culture medium and a non-toxic chelating agent.

2. The serum-free growth medium of claim 1, wherein the chelating agent comprises EDTA and citrate buffer.

3. The serum-free growth medium of claim 2, further comprising Fe—EDTA and citrate buffer in a molar ratio of about 1 part Fe—EDTA: 3 parts citrate buffer.

4. The serum-free growth medium of claims 1 or 2, further comprising aurintricarboxylic acid in a concentration between about 0.1-10 $\mu$M.

5. The serum-free growth medium of claim 10, comprising aurintricarboxylic acid in a concentration between about 1-5 $\mu$M.

6. The serum-free growth medium of claim 10, comprising aurintricarboxylic acid in a concentration of about 3 $\mu$M.

7. The serum-free growth medium of claim 1 further comprising trace elements and, wherein the chelating agent is an alkali-metal-EDTA in a chelated form.

8. The serum-free growth medium of claim 7, wherein the alkali metal—EDTA is $Na_2$—EDTA or $K_2$—EDTA.

9. The serum-free growth medium of claim 8, wherein the alkali-metal—EDTA is $Na_2$—EDTA.

10. The serum-free growth medium of claim 7, wherein the trace elements comprise Zn, Cu, Mn, Ni, Al, Cr, Co and Se.

11. The serum-free growth medium of claim 1 wherein the iron-containing base cell culture medium comprises a modified RPMI 1640 media with HEPES and $NaHCO_3$.

12. A serum-free growth medium additive comprising:
    a non-toxic iron chelate; and
    aurintricarboxylic acid, wherein the concentration of aurintricarboxylic acid is between about 0.1-10 mM, and which has a pH in the range of about 4.5-5.0.

13. The serum-free growth medium additive of claim 12, further cmoprising about 2.4-3.6 mM Fe-EDTA, about 0.1-10.0 mM aurintricarboxylic acid, about 0.8-1.2 mM $Na_2$—EDTA, about 12-18 mM citric acid and about 20-30 mM $Na_3$-citrate.

14. The serum-free growth medium additive of claim 12, further defined as comprising about 3 mM aurintricarboxylic acid.

15. The serum-free growth medium additive of claim 12, further defined as a dry-matter composition.

16. The serum-free growth medium additive of claim 12, wherein the iron chelate is Fe—EDTA.

17. The serum-free growth medium additive of claim 16, further comprising a citrate buffer, wherein the molar ratio of citrate buffer to Fe—EDTA is 10:1.

18. A serum-free growth medium additive comprising:
    a non-toxic iron chelating agent; and
    about 0.1-10.0 mM aurintricarboxylic acid.

19. The serum-free growth medium additive of claim 18 further comprising between about 2.4—3.6 mM aurintricarboxylic acid.

20. The serum-free growth medium additive of claim 18 fuerther comprising about 3 mM aurintricarboxylic acid.

21. The serum-free growth medium additive of claim 18 further comprising:
    about 2.4-3.6 mM Fe—EDTA;
    about 0.8-1.2 mM $Na_2$—EDTA;
    about 12-18 mM citric acid; and
    about 20-30 mM $Na_3$-citrate.

22. The serum-free growth medium additive of claim 18 further comprising trace elements.

23. The serum-free growth medium additive of claim 22, wherein the trace elements comprise $Zn^{2+}$, $Cu^{2+}$, $Mn^{2+}$, $Ni^{2+}$, $Al^{3+}$, $Cr^{3+}$, $Co^{2+}$ and $Se^{4+}$.

24. The serum-free growth medium additive of claim 18 further comprising:
    0.08-0.12 millimolar $Zn^{2+}$;
    16-24 micromolar $Cu^{2+}$;
    1.6-2.4 micromolar $Al^{3+}$;
    0.8-1.2 micromolar $Cr^{3+}$;
    0.16-0.24 micromolar $Co^{2+}$;
    8-12 micromolar $Se^{4+}$;
    0.2 micromolar $Ni^{2+}$; and
    1.0 micromolar $Mn^{2+}$.

25. The serum-free growth medium additive of claim 18 further comprising growth factors.

26. The serum-free growth medium additive of claim 25, wherein the growth factors are selected from the group consisting of pluronic F68, D-glucose, L-glutamine, Na-pyruvate, insulin and ethanolamine.

27. The serum-free growth medium comprising a non-toxic iron chelate; about 0.1-10 $\mu$M aurintricarboxylic acid; and an iron-containing cell culture base medium comprising RPMI 1640 media, HEPES and $NaHCO_3$.

28. A kit useful for the detection of toxic substances or impurities in a eukaryotic cell culture medium comprising:
    a carrier being compartmentalized to receive at least two container means and at least one culture plate in close confinment therein;
    a culture plate comprising a plurality of wells;
    a first containter means containing hybridoma cells, ECACC #86 112002: and
    a second container means containing a serum-free growth medium additive comprising aurintricarboxylic acid, Fe—EDTA and $Na_3$-citrate.

29. The kit of claim 28, wherein the carrier and container means comprise plastic or other material suitable for containing biological reagents.

30. A method for detecting the presence of a toxic substance in a test material comprising:
    adding the test material to a volume of serum-free, iron containing cell culture medium comprising aurintricarboyxlic acid and an iron chelating agent in a base cell culture medium to form a toxin-detecting concentration of a combination cell culture medium;
    adding hybridoma cells to the combination cell culture medium to form a test culture;
    preparing a control culture cmprising hybridoma cells and an iron-containing, serum-free cell culture medium comprising aurintricarboxylic acid and an iron chelating agent in a base cell culture medium;
    incubating the test culture and the control culture; and
    comparing hybridoma growth in the test culture to growth in the control culture;
    wherein greater hybridoma growth in the control culture than in the test culture indicates the presence of a toxic substance in the test material.

31. A method for testing for the presence of a toxic substance in an unknown cell culture medium comprising:
- preparing a serum-free cell culture medium comprising aurintricarboxylic acid, iron and a chelating agent in a sufficient volume of a base cell culture medium to prepare a test culture and a control culture;
- adding to a portion of the serum-free cell culture medium a volume of the unknown cell culture medium in about a 1:1 ratio to form a combination cell culture medium;
- adding a number of hybridoma cells ECACC #86 112001 to the combination cell culture medium to form a test culture;
- adding a number of hybridoma cells ECACC #86 112001 to a volume of the serum-free cell culture medium to form a control culture;
- incubating the test culture and the control culture for a period of time;
- counting the number of hybridoma cells present in the test culture and the number of hybridoma cells in the control culture after incubation; and
- comparing the number of hybridoma cells in the test culture to the number of hybridoma cells in the cotnrol culture;

wherein an equal number of hybridoma cells in the test culture to the number of hybridoma cells in the control culture indicates the absence of a toxic substance in the test material.

32. The kit of claim 28 or method of claim 31, wherein said iron-containing base cell culture medium is a modified RPMI 1640 medium comprising about 2.2 g/L $NaHCO_3$ and about 15 mM HEPES.

33. The method of claim 30 or 31, wherein the number of hybridoma cells added to the test culture and the control culture is approximatley 30,000 cells/ml of cluture medium.

34. The method of claim 30 or 31, wherein the period of time for incubation is about 4 days.

35. The method of claim 30 or 32, wherien the serum-free cell culture medium further comprises
- about 3 micromolar Fe;
- about 1 nanomolar Mn;
- about 1 nanomolar Cr;
- about 0.1 micromolar Zn;
- about 0.2 nanomolar Ni;
- about 0.2 nanomolar Co;
- about 20 nanomolar Cu;
- about 2 nanomolar Al; and
- about 10 nanomolar Se.

36. The kit of claim 28 or the method of claim 30 or 31, wherein the toxic substance to be detected is selected from the group consisting of:
- antibodies
- lidocaine
- heavy metals
- caffeine
- phenolic compounds
- ethylene glycol
- detergents
- orphenadrine hydrochloride
- bacterial toxins
- formalin
- hydrazine
- cetyl-pyridiniumchloride 37. The kit of claim 35 or the method of claim 36 or 37, wherein the toxic substance is a bacterial toxin comprising botulin toxin or a diphtheria toxin.

38. A method for preparing a serum-free cell culture medium comprising preparing a solution A containing
- about 20 mg/ml Pluronic F 68;
- about 4 mM EDTA;
- about 3 mM Fe;
- about 40 mM sodium citrate/citric acid;
- about 3 mM aurintricarboxylic acid;
- about 0.8–0.12 millimolar $Zn^{2+}$;
- about 16–24 micromolar $Cu^{2+}$;
- about 1.6–2.4 micromolar $Al^{3+}$;
- 0.8–1.2 micromolar $Cr^{3+}$;
- 0.16–0.24 micromolar $Co^{2+}$;
- 8–12 micromolar $Se^{4+}$;
- 0.2 micromolar $Ni^{2+}$;
- 1.0 micromolar $Mn^{2+}$; and preparing a solution B containing about 0.5 mg/ml insulin;

preparing a solution C containing about 20 1 mM ethanolamine; and mixing an appropriate volume of solution A, solution B and solution C in a cell culture base medium to form a serum-free cell culture medium.

39. The method of claim 38, wherein the serum-free cell culture medium is further defined as comprising compounds selected from the group consisting of:
- D-glucose;
- L-glutamine; and
- Na-pyruvate.

40. A method for preparing a serum-free, iron-chelating growth medium comprising:
- preparing a volume of iron-containing base cell culture medium;
- combining a volume of the serum-free growth medium additive according to claim 14 with an iron-containing base cell culture medium to form a cell-ready complete serum-free culture medium; and
- adjusting the pH of the cell-ready complete serum-free culture medium to a pH of between 7.0 and 7.8.

41. The method of claim 40, wherein the iron-containing base cell culture medium is a modified RPMI 1640 medium comprising RPMI 1640, with HEPES and $NaHCO_3$.

42. The method of claim 41, wherein the modified RPMI 1640 medium comprises RPMI 1640 base medium with 2.5 g/l $NaHCO_3$ and 20 mM HEPES.

43. A cell culture medium transferrin-replacement comprising:
- aurintricarboxylic acid;
- citrate buffer; and
- EDTA.

44. The cell culture medium transferrin-replacement of claim 43 further comprising aurintricarboxylic acid in a concentration between 0.1–10.0 mM.

45. The cell culture medium transferrin-replacement of claim 43 further comprising aurintricarboxylic acid in a concentration between 2.4–3.6 mM.

46. The cell culture medium transferrin-replacement of claim 43 further comprising aurintricarboxylic acid in a concentration of about 3 mM.

47. The cell culture medium transferrin-replacement of claim 43 further comprising citrate buffer and EDTA in a molar ratio of at least about 3:1.

48. The cell culture medium transferrin-replacement of claim 43 further comprising:
- about 2.4–3.6 millimolar Fe-EDTA;

UNITED STATES PATENT AND TRADEMARK OFFICE
CERTIFICATE OF CORRECTION

PATENT NO. : 5,045,454

DATED : September 3, 1991

INVENTOR(S) : Kjell Bertheussen

It is certified that error appears in the above-identified patent and that said Letters Patent is hereby corrected as shown below:

On the title page, delete the first name of the inventor "Kiell" and insert therefor --Kjell--.

In claim 13, column 23, line 45, delete the word "cmoprising" and insert therefor --comprising--.

In claim 20, column 23, line 67, delete the word fuerther" and insert therefor --further--.

In claim 24, column 24, line 14, delete "2n$^{2+}$ " and insert therefore --Zn$^{2-}$--

In claim 28, column 24, line 38, delete the word "confinment" and insert therefor --confinement--.

In claim 28, column 24, line 40, delete the word "containter" and insert therefor --container--.

In claim 30, column 24, line 52, delete the word "aurintricarboyxlic" and insert therefor --aurintricarboxylic--.

In claim 30, column 24, line 58, delete the word "cmprising" and insert therefor --comprising--.

UNITED STATES PATENT AND TRADEMARK OFFICE
CERTIFICATE OF CORRECTION

PATENT NO. : 5,045,454
DATED : September 3, 1991
INVENTOR(S) : Kjell Bertheussen It is certified that error appears in the above-identified patent and that said Letters Patent is hereby corrected as shown below:

In claim 37, column 26, line 1, delete "35" and insert therefor --28--.

In claim 37, column 26, line 1, delete "36" and insert therefor --30--.

In claim 37, column 26, line 2, delete "37" and insert therefor --31--.

In claim 38, column 26, line 21, delete "1".

In claim 40, column 26, line 32-33, delete the word "chelating" and insert therefor --containing--.

In claim 49, column 27, line 8, after the word "in", insert the words --a volume of--.

Signed and Sealed this

Sixteenth Day of February, 1993

Attest:

STEPHEN G. KUNIN

Attesting Officer  Acting Commissioner of Patents and Trademarks